(12) United States Patent
Tabor et al.

(10) Patent No.: US 9,149,358 B2
(45) Date of Patent: Oct. 6, 2015

(54) DELIVERY SYSTEMS FOR PROSTHETIC HEART VALVES

(75) Inventors: Charles Tabor, Shoreview, MN (US); Paul Rothstein, Elk River, MN (US); Eliot Bloom, Hopkinton, NH (US)

(73) Assignee: Medtronic, Inc., Minneapolis, MN (US)

( * ) Notice: Subject to any disclaimer, the term of this patent is extended or adjusted under 35 U.S.C. 154(b) by 856 days.

(21) Appl. No.: 12/358,489

(22) Filed: Jan. 23, 2009

(65) Prior Publication Data
US 2009/0192586 A1 Jul. 30, 2009

Related U.S. Application Data

(60) Provisional application No. 61/062,207, filed on Jan. 24, 2008.

(51) Int. Cl.
*A61F 2/06* (2013.01)
*A61F 2/24* (2006.01)
*A61F 2/95* (2013.01)

(52) U.S. Cl.
CPC ............. *A61F 2/2412* (2013.01); *A61F 2/2427* (2013.01); *A61F 2/2436* (2013.01); *A61F 2/95* (2013.01); *A61F 2/2418* (2013.01); *A61F 2/2439* (2013.01); *A61F 2002/9505* (2013.01); *A61F 2002/9511* (2013.01); *A61F 2250/0098* (2013.01)

(58) Field of Classification Search
CPC .............. A61F 2/95; A61F 2002/9505; A61F 2002/9511; A61F 2002/9665; A61F 2220/0025; A61F 2220/0091; A61F 2250/0062; A61F 2/2427; A61F 2/2439; A61F 2002/9517; A61F 2002/9534; A61F 2/962; A61F 2/966; A61F 2002/011; A61F 2/2466

USPC ............ 623/1.11, 1.23, 1.24, 1.26–1.28, 2.11
See application file for complete search history.

(56) References Cited

U.S. PATENT DOCUMENTS

| | | | |
|---|---|---|---|
| 3,334,629 A | * | 8/1967 | Cohn ............................. 606/194 |
| 3,409,013 A | | 11/1968 | Berry |
| 3,540,431 A | | 11/1970 | Mobin-Uddin |
| 3,587,115 A | | 6/1971 | Shiley |

(Continued)

FOREIGN PATENT DOCUMENTS

| CN | 2007-100074433 | 8/2007 |
|---|---|---|
| DE | 3640745 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — David Eastwood
*Assistant Examiner* — Erin Colello

(57) ABSTRACT

A delivery system for delivery of an implantable stented device to a body lumen, the device having a plurality of structures at its proximal end, wherein the delivery system comprises a first body portion removably attached to a second body portion and wherein the second body portion includes a plurality of attachment components at its distal end for attachment to the plurality of structures at the proximal end of the device.

13 Claims, 7 Drawing Sheets

(56) References Cited

U.S. PATENT DOCUMENTS

| | | | |
|---|---|---|---|
| 3,628,535 A * | 12/1971 | Ostrowsky et al. ............ 604/303 |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,901 A | 10/1988 | Baykut |
| 4,787,899 A | 11/1988 | Lazarus |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,913,141 A * | 4/1990 | Hillstead ..................... 623/1.11 |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,433,723 A * | 7/1995 | Lindenberg et al. .......... 606/198 |
| 5,443,446 A | 8/1995 | Shturman |
| 5,443,500 A * | 8/1995 | Sigwart ...................... 623/1.17 |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,749,921 A * | 5/1998 | Lenker et al. ................ 623/1.42 |
| 5,766,151 A | 6/1998 | Valley et al. |
| 5,776,142 A * | 7/1998 | Gunderson .................. 623/1.11 |
| 5,782,809 A | 7/1998 | Umeno et al. |
| 5,800,455 A * | 9/1998 | Palermo et al. .............. 606/191 |
| 5,800,456 A | 9/1998 | Maeda et al. |
| 5,800,508 A | 9/1998 | Goicoechea et al. |
| 5,807,405 A * | 9/1998 | Vanney et al. ............... 623/2.11 |
| 5,817,126 A | 10/1998 | Imran |
| 5,824,041 A * | 10/1998 | Lenker et al. ................ 606/195 |
| 5,824,043 A | 10/1998 | Cottone, Jr. |
| 5,824,053 A * | 10/1998 | Khosravi et al. ............. 623/1.15 |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A * | 1/1999 | Bessler et al. ................ 623/2.38 |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,944,750 A * | 8/1999 | Tanner et al. ................ 623/1.23 |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,984,959 A * | 11/1999 | Robertson et al. ........... 623/2.11 |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |

(56) References Cited

U.S. PATENT DOCUMENTS

| | | | |
|---|---|---|---|
| 6,042,607 A | 3/2000 | Williamson, IV | |
| 6,051,014 A | 4/2000 | Jang | |
| 6,059,809 A | 5/2000 | Amor et al. | |
| 6,110,201 A | 8/2000 | Quijano et al. | |
| 6,146,366 A | 11/2000 | Schachar | |
| 6,159,239 A | 12/2000 | Greenhalgh | |
| 6,162,208 A | 12/2000 | Hipps | |
| 6,162,245 A | 12/2000 | Jayaraman | |
| 6,168,614 B1 | 1/2001 | Andersen et al. | |
| 6,168,616 B1* | 1/2001 | Brown, III | 623/1.11 |
| 6,168,618 B1* | 1/2001 | Frantzen | 623/1.12 |
| 6,171,335 B1 | 1/2001 | Wheatley et al. | |
| 6,200,336 B1 | 3/2001 | Pavcnik et al. | |
| 6,203,550 B1 | 3/2001 | Olson | |
| 6,210,408 B1 | 4/2001 | Chandrasekaran et al. | |
| 6,214,039 B1* | 4/2001 | Banas et al. | 623/1.13 |
| 6,218,662 B1 | 4/2001 | Tchakarov et al. | |
| 6,221,006 B1 | 4/2001 | Dubrul et al. | |
| 6,221,091 B1 | 4/2001 | Khosravi | |
| 6,241,757 B1 | 6/2001 | An et al. | |
| 6,245,102 B1 | 6/2001 | Jayaraman | |
| 6,248,116 B1 | 6/2001 | Chevilon | |
| 6,254,630 B1* | 7/2001 | Inoue | 623/1.15 |
| 6,258,114 B1 | 7/2001 | Konya et al. | |
| 6,258,115 B1 | 7/2001 | Dubrul | |
| 6,258,120 B1 | 7/2001 | McKenzie et al. | |
| 6,277,555 B1 | 8/2001 | Duran et al. | |
| 6,299,637 B1 | 10/2001 | Shaolian et al. | |
| 6,302,906 B1 | 10/2001 | Goicoechea et al. | |
| 6,309,382 B1 | 10/2001 | Garrison et al. | |
| 6,309,417 B1 | 10/2001 | Spence et al. | |
| 6,338,735 B1 | 1/2002 | Stevens | |
| 6,348,063 B1 | 2/2002 | Yassour et al. | |
| 6,350,277 B1 | 2/2002 | Kocur | |
| 6,352,708 B1 | 3/2002 | Duran et al. | |
| 6,371,970 B1 | 4/2002 | Khosravi et al. | |
| 6,371,979 B1* | 4/2002 | Beyar et al. | 623/1.12 |
| 6,371,983 B1 | 4/2002 | Lane | |
| 6,379,383 B1 | 4/2002 | Palmaz et al. | |
| 6,380,457 B1 | 4/2002 | Yurek et al. | |
| 6,398,807 B1 | 6/2002 | Chouinard et al. | |
| 6,409,750 B1 | 6/2002 | Hyodoh et al. | |
| 6,425,916 B1 | 7/2002 | Garrison et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,303 B1 | 10/2002 | Amplatz et al. | |
| 6,475,239 B1 | 11/2002 | Campbell et al. | |
| 6,482,228 B1 | 11/2002 | Norred | |
| 6,488,704 B1 | 12/2002 | Connelly et al. | |
| 6,494,909 B2 | 12/2002 | Greenhalgh | |
| 6,503,272 B2 | 1/2003 | Duerig et al. | |
| 6,508,833 B2 | 1/2003 | Pavcnik et al. | |
| 6,517,548 B2* | 2/2003 | Lorentzen Cornelius et al. | 606/108 |
| 6,527,800 B1 | 3/2003 | McGuckin, Jr. et al. | |
| 6,530,949 B2 | 3/2003 | Konya et al. | |
| 6,530,952 B2 | 3/2003 | Vesely | |
| RE38,091 E* | 4/2003 | Strecker | 623/1.12 |
| 6,562,031 B2 | 5/2003 | Chandrasekaran et al. | |
| 6,562,058 B2 | 5/2003 | Seguin et al. | |
| 6,569,196 B1 | 5/2003 | Vesely | |
| 6,582,460 B1* | 6/2003 | Cryer | 623/1.11 |
| 6,585,758 B1 | 7/2003 | Chouinard et al. | |
| 6,592,546 B1 | 7/2003 | Barbut et al. | |
| 6,605,104 B2* | 8/2003 | Sato et al. | 606/206 |
| 6,605,112 B1 | 8/2003 | Moll et al. | |
| 6,613,077 B2 | 9/2003 | Gilligan et al. | |
| 6,622,604 B1 | 9/2003 | Chouinard et al. | |
| 6,635,068 B1 | 10/2003 | Dubrul et al. | |
| 6,635,079 B2* | 10/2003 | Unsworth et al. | 623/1.11 |
| 6,652,571 B1 | 11/2003 | White et al. | |
| 6,652,578 B2 | 11/2003 | Bailey et al. | |
| 6,656,213 B2 | 12/2003 | Solem | |
| 6,663,663 B2 | 12/2003 | Kim et al. | |
| 6,666,881 B1* | 12/2003 | Richter et al. | 623/1.12 |
| 6,669,724 B2 | 12/2003 | Park et al. | |
| 6,673,089 B1 | 1/2004 | Yassour et al. | |
| 6,673,109 B2 | 1/2004 | Cox | |
| 6,676,698 B2 | 1/2004 | McGuckin, Jr. et al. | |
| 6,682,558 B2 | 1/2004 | Tu et al. | |
| 6,682,559 B2 | 1/2004 | Myers et al. | |
| 6,685,739 B2 | 2/2004 | DiMatteo et al. | |
| 6,689,144 B2 | 2/2004 | Gerberding | |
| 6,689,164 B1 | 2/2004 | Seguin | |
| 6,692,512 B2 | 2/2004 | Jang | |
| 6,692,513 B2 | 2/2004 | Streeter et al. | |
| 6,695,878 B2 | 2/2004 | McGuckin, Jr. et al. | |
| 6,702,851 B1 | 3/2004 | Chinn et al. | |
| 6,719,789 B2 | 4/2004 | Cox | |
| 6,730,118 B2 | 5/2004 | Spenser et al. | |
| 6,730,377 B2 | 5/2004 | Wang | |
| 6,733,525 B2 | 5/2004 | Yang et al. | |
| 6,736,846 B2 | 5/2004 | Cox | |
| 6,752,828 B2 | 6/2004 | Thornton | |
| 6,758,855 B2 | 7/2004 | Fulton, III et al. | |
| 6,769,434 B2 | 8/2004 | Liddicoat et al. | |
| 6,776,791 B1* | 8/2004 | Stallings et al. | 623/1.11 |
| 6,786,925 B1 | 9/2004 | Schoon et al. | |
| 6,790,229 B1 | 9/2004 | Berreklouw | |
| 6,790,230 B2 | 9/2004 | Beyersdorf et al. | |
| 6,792,979 B2 | 9/2004 | Konya et al. | |
| 6,797,002 B2 | 9/2004 | Spence | |
| 6,821,297 B2* | 11/2004 | Snyders | 623/2.18 |
| 6,830,575 B2 | 12/2004 | Stenzel et al. | |
| 6,830,584 B1 | 12/2004 | Seguin | |
| 6,830,585 B1 | 12/2004 | Artof | |
| 6,846,325 B2 | 1/2005 | Liddicoat | |
| 6,866,650 B2 | 3/2005 | Stevens | |
| 6,872,223 B2 | 3/2005 | Roberts | |
| 6,875,231 B2 | 4/2005 | Anduiza et al. | |
| 6,883,522 B2 | 4/2005 | Spence et al. | |
| 6,887,266 B2 | 5/2005 | Williams et al. | |
| 6,890,330 B2 | 5/2005 | Streeter et al. | |
| 6,893,460 B2 | 5/2005 | Spenser et al. | |
| 6,896,690 B1 | 5/2005 | Lambrecht et al. | |
| 6,908,481 B2 | 6/2005 | Cribier | |
| 6,913,600 B2 | 7/2005 | Valley et al. | |
| 6,916,335 B2* | 7/2005 | Kanji | 623/1.11 |
| 6,929,653 B2 | 8/2005 | Strecter | |
| 6,936,066 B2 | 8/2005 | Palmaz et al. | |
| 6,939,365 B1 | 9/2005 | Fogarty et al. | |
| 6,951,571 B1 | 10/2005 | Srivastava | |
| 6,974,474 B2 | 12/2005 | Pavcnik et al. | |
| 6,974,476 B2 | 12/2005 | McGuckin et al. | |
| 6,986,742 B2 | 1/2006 | Hart et al. | |
| 6,989,027 B2 | 1/2006 | Allen et al. | |
| 6,989,028 B2 | 1/2006 | Lashinski et al. | |
| 6,991,649 B2 | 1/2006 | Sievers | |
| 7,018,401 B1 | 3/2006 | Hyodoh et al. | |
| 7,022,132 B2* | 4/2006 | Kocur | 623/1.11 |
| 7,022,133 B2* | 4/2006 | Yee et al. | 623/1.11 |
| 7,041,128 B2 | 5/2006 | McGuckin, Jr. et al. | |
| 7,044,966 B2* | 5/2006 | Svanidze et al. | 623/2.1 |
| 7,048,014 B2 | 5/2006 | Hyodoh et al. | |
| 7,097,659 B2 | 8/2006 | Woolfson et al. | |
| 7,101,396 B2 | 9/2006 | Artof et al. | |
| 7,105,016 B2 | 9/2006 | Shiu et al. | |
| 7,115,141 B2 | 10/2006 | Menz et al. | |
| 7,128,759 B2 | 10/2006 | Osborne et al. | |
| 7,147,663 B1 | 12/2006 | Berg et al. | |
| 7,153,324 B2 | 12/2006 | Case et al. | |
| 7,160,319 B2 | 1/2007 | Chouinard et al. | |
| 7,175,656 B2 | 2/2007 | Khairkhahan | |
| 7,186,265 B2 | 3/2007 | Sharkawy et al. | |
| 7,195,641 B2 | 3/2007 | Palmaz et al. | |
| 7,198,646 B2 | 4/2007 | Figulla et al. | |
| 7,201,761 B2 | 4/2007 | Woolfson et al. | |
| 7,201,772 B2 | 4/2007 | Schwammenthal et al. | |
| 7,252,680 B2* | 8/2007 | Freitag | 623/1.12 |
| 7,252,682 B2 | 8/2007 | Seguin | |
| 7,300,457 B2 | 11/2007 | Palmaz | |
| 7,300,463 B2 | 11/2007 | Liddicoat | |

(56) References Cited

U.S. PATENT DOCUMENTS

| | | | |
|---|---|---|---|
| 7,316,706 B2 | 1/2008 | Bloom et al. | |
| 7,329,278 B2 | 2/2008 | Seguin | |
| 7,335,218 B2 | 2/2008 | Wilson et al. | |
| 7,338,520 B2 | 3/2008 | Bailey et al. | |
| 7,374,571 B2 | 5/2008 | Pease et al. | |
| 7,377,938 B2 | 5/2008 | Sarac et al. | |
| 7,381,218 B2 | 6/2008 | Schreck | |
| 7,384,411 B1 | 6/2008 | Condado | |
| 7,419,501 B2* | 9/2008 | Chiu et al. | 623/1.12 |
| 7,429,269 B2 | 9/2008 | Schwammenthal et al. | |
| 7,442,204 B2 | 10/2008 | Schwammenthal et al. | |
| 7,462,191 B2 | 12/2008 | Spenser et al. | |
| 7,470,284 B2 | 12/2008 | Lambrecht et al. | |
| 7,481,838 B2 | 1/2009 | Carpentier et al. | |
| 7,544,206 B2* | 6/2009 | Cohn | 623/2.11 |
| 7,547,322 B2 | 6/2009 | Sarac et al. | |
| 7,556,646 B2 | 7/2009 | Yang et al. | |
| 7,651,521 B2* | 1/2010 | Ton et al. | 623/1.12 |
| 7,666,219 B2* | 2/2010 | Rasmussen et al. | 623/1.12 |
| 7,682,390 B2 | 3/2010 | Seguin | |
| 7,722,666 B2* | 5/2010 | Lafontaine | 623/2.11 |
| 7,758,589 B2* | 7/2010 | Ortiz et al. | 606/108 |
| 7,780,725 B2* | 8/2010 | Haug et al. | 623/2.17 |
| 7,780,726 B2 | 8/2010 | Seguin | |
| 7,785,361 B2* | 8/2010 | Nikolchev et al. | 623/1.11 |
| 7,806,919 B2 | 10/2010 | Bloom et al. | |
| 7,837,643 B2* | 11/2010 | Levine et al. | 604/8 |
| 7,862,602 B2* | 1/2011 | Licata et al. | 623/1.11 |
| 8,136,659 B2* | 3/2012 | Salahieh et al. | 206/210 |
| 2001/0001314 A1 | 5/2001 | Davison et al. | |
| 2001/0002445 A1* | 5/2001 | Vesely | 623/2.11 |
| 2001/0007956 A1 | 7/2001 | Letac et al. | |
| 2001/0010017 A1 | 7/2001 | Letac et al. | |
| 2001/0011189 A1 | 8/2001 | Drasler et al. | |
| 2001/0021872 A1 | 9/2001 | Bailey et al. | |
| 2001/0025196 A1 | 9/2001 | Chinn et al. | |
| 2001/0032013 A1 | 10/2001 | Marton | |
| 2001/0037142 A1* | 11/2001 | Stelter et al. | 623/1.13 |
| 2001/0039450 A1 | 11/2001 | Pavcnik et al. | |
| 2001/0041928 A1 | 11/2001 | Pavcnik et al. | |
| 2001/0044647 A1 | 11/2001 | Pinchuk et al. | |
| 2001/0047150 A1* | 11/2001 | Chobotov | 604/107 |
| 2001/0049550 A1* | 12/2001 | Martin et al. | 623/1.13 |
| 2002/0010508 A1 | 1/2002 | Chobotov | |
| 2002/0029014 A1 | 3/2002 | Jayaraman | |
| 2002/0032480 A1 | 3/2002 | Spence et al. | |
| 2002/0032481 A1 | 3/2002 | Gabbay | |
| 2002/0035396 A1 | 3/2002 | Heath | |
| 2002/0042650 A1 | 4/2002 | Vardi et al. | |
| 2002/0052651 A1 | 5/2002 | Myers et al. | |
| 2002/0058995 A1 | 5/2002 | Stevens | |
| 2002/0065545 A1* | 5/2002 | Leonhardt et al. | 623/1.1 |
| 2002/0072789 A1 | 6/2002 | Hackett et al. | |
| 2002/0091439 A1* | 7/2002 | Baker et al. | 623/1.36 |
| 2002/0095209 A1 | 7/2002 | Zadno-Azizi et al. | |
| 2002/0099439 A1 | 7/2002 | Schwartz et al. | |
| 2002/0103533 A1 | 8/2002 | Langberg et al. | |
| 2002/0107565 A1 | 8/2002 | Greenhalgh | |
| 2002/0111674 A1 | 8/2002 | Chouinard et al. | |
| 2002/0120277 A1 | 8/2002 | Hauschild et al. | 606/108 |
| 2002/0120323 A1* | 8/2002 | Thompson et al. | 623/1.11 |
| 2002/0123802 A1 | 9/2002 | Snyders | |
| 2002/0133183 A1 | 9/2002 | Lentz et al. | |
| 2002/0138138 A1* | 9/2002 | Yang | 623/2.18 |
| 2002/0151970 A1 | 10/2002 | Garrison et al. | |
| 2002/0161392 A1 | 10/2002 | Dubrul | |
| 2002/0161394 A1 | 10/2002 | Macoviak et al. | |
| 2002/0188341 A1* | 12/2002 | Elliott | 623/1.1 |
| 2002/0193871 A1 | 12/2002 | Beyersdorf et al. | |
| 2003/0004560 A1* | 1/2003 | Chobotov et al. | 623/1.11 |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0028247 A1 | 2/2003 | Cali | |
| 2003/0036791 A1 | 2/2003 | Philipp et al. | |
| 2003/0040771 A1 | 2/2003 | Hyodoh et al. | |
| 2003/0040772 A1 | 2/2003 | Hyodoh et al. | |
| 2003/0040792 A1 | 2/2003 | Gabbay | |
| 2003/0050684 A1* | 3/2003 | Abrams et al. | 623/1.11 |
| 2003/0050694 A1 | 3/2003 | Yang et al. | |
| 2003/0055495 A1 | 3/2003 | Pease et al. | |
| 2003/0065386 A1 | 4/2003 | Weadock | |
| 2003/0069492 A1 | 4/2003 | Abrams et al. | |
| 2003/0109924 A1 | 6/2003 | Cribier | |
| 2003/0125795 A1 | 7/2003 | Pavcnik et al. | |
| 2003/0130726 A1 | 7/2003 | Thorpe et al. | |
| 2003/0130729 A1 | 7/2003 | Paniagua et al. | |
| 2003/0135257 A1* | 7/2003 | Taheri | 623/1.11 |
| 2003/0139804 A1 | 7/2003 | Hankh et al. | |
| 2003/0149475 A1 | 8/2003 | Hyodoh et al. | |
| 2003/0149476 A1 | 8/2003 | Damm et al. | |
| 2003/0149478 A1 | 8/2003 | Figulla et al. | |
| 2003/0153974 A1 | 8/2003 | Spenser et al. | |
| 2003/0181850 A1 | 9/2003 | Diamond et al. | |
| 2003/0191519 A1 | 10/2003 | Lombardi et al. | |
| 2003/0199913 A1 | 10/2003 | Dubrul et al. | |
| 2003/0199963 A1 | 10/2003 | Tower et al. | |
| 2003/0199971 A1 | 10/2003 | Tower et al. | |
| 2003/0212410 A1 | 11/2003 | Stenzel et al. | |
| 2003/0212454 A1 | 11/2003 | Scott et al. | |
| 2003/0225445 A1 | 12/2003 | Derus et al. | |
| 2003/0233140 A1* | 12/2003 | Hartley et al. | 623/1.11 |
| 2004/0019374 A1 | 1/2004 | Hojeibane et al. | |
| 2004/0034411 A1* | 2/2004 | Quijano et al. | 623/2.11 |
| 2004/0039436 A1 | 2/2004 | Spenser et al. | |
| 2004/0049224 A1 | 3/2004 | Buehlmann et al. | |
| 2004/0049262 A1 | 3/2004 | Obermiller et al. | |
| 2004/0049266 A1 | 3/2004 | Anduiza et al. | |
| 2004/0059413 A1* | 3/2004 | Argento | 623/2.11 |
| 2004/0082904 A1 | 4/2004 | Houde et al. | |
| 2004/0088045 A1 | 5/2004 | Cox | |
| 2004/0092858 A1 | 5/2004 | Wilson et al. | |
| 2004/0092989 A1 | 5/2004 | Wilson et al. | |
| 2004/0093005 A1 | 5/2004 | Durcan | |
| 2004/0093060 A1 | 5/2004 | Seguin et al. | |
| 2004/0093075 A1 | 5/2004 | Kuehn | |
| 2004/0097788 A1 | 5/2004 | Mourlas et al. | |
| 2004/0098112 A1 | 5/2004 | DiMatteo et al. | |
| 2004/0106976 A1 | 6/2004 | Bailey et al. | |
| 2004/0106990 A1 | 6/2004 | Spence et al. | |
| 2004/0111096 A1 | 6/2004 | Tu et al. | |
| 2004/0116951 A1 | 6/2004 | Rosengart | |
| 2004/0117004 A1 | 6/2004 | Osborne et al. | |
| 2004/0122468 A1 | 6/2004 | Yodfat et al. | |
| 2004/0122514 A1 | 6/2004 | Fogarty et al. | |
| 2004/0122516 A1 | 6/2004 | Fogarty | |
| 2004/0127979 A1 | 7/2004 | Wilson | |
| 2004/0138742 A1 | 7/2004 | Myers et al. | |
| 2004/0138743 A1 | 7/2004 | Myers et al. | |
| 2004/0153146 A1 | 8/2004 | Lashinski et al. | |
| 2004/0167573 A1 | 8/2004 | Williamson | |
| 2004/0167620 A1 | 8/2004 | Ortiz | |
| 2004/0186514 A1* | 9/2004 | Swain et al. | 606/224 |
| 2004/0186563 A1* | 9/2004 | Lobbi | 623/2.11 |
| 2004/0193261 A1 | 9/2004 | Berreklouw | |
| 2004/0210240 A1 | 10/2004 | Saint | |
| 2004/0210304 A1* | 10/2004 | Seguin et al. | 623/2.11 |
| 2004/0210307 A1 | 10/2004 | Khairkhahan | |
| 2004/0215333 A1 | 10/2004 | Duran | |
| 2004/0215339 A1 | 10/2004 | Drasler et al. | |
| 2004/0220655 A1* | 11/2004 | Swanson et al. | 623/1.11 |
| 2004/0225353 A1 | 11/2004 | McGuckin, Jr. | |
| 2004/0225354 A1 | 11/2004 | Allen | |
| 2004/0254636 A1 | 12/2004 | Flagle et al. | |
| 2004/0260383 A1* | 12/2004 | Stelter et al. | 623/1.11 |
| 2004/0260389 A1 | 12/2004 | Case et al. | |
| 2004/0260390 A1 | 12/2004 | Douk et al. | |
| 2004/0267357 A1 | 12/2004 | Allen et al. | |
| 2005/0010246 A1 | 1/2005 | Streeter | |
| 2005/0010285 A1 | 1/2005 | Lambrecht et al. | |
| 2005/0010287 A1 | 1/2005 | Macoviak | |
| 2005/0015112 A1 | 1/2005 | Cohn et al. | |
| 2005/0027348 A1 | 2/2005 | Case et al. | |
| 2005/0033398 A1 | 2/2005 | Seguin | |

(56) References Cited

U.S. PATENT DOCUMENTS

| | | |
|---|---|---|
| 2005/0043790 A1 | 2/2005 | Seguin |
| 2005/0049667 A1* | 3/2005 | Arbefeuille et al. ......... 623/1.11 |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1* | 4/2005 | Rasmussen et al. ......... 623/1.11 |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1* | 6/2005 | Salahieh et al. ............ 623/2.38 |
| 2005/0143807 A1 | 6/2005 | Pavcnik et al. |
| 2005/0143809 A1* | 6/2005 | Salahieh et al. ............ 623/2.11 |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1* | 9/2005 | Realyvasquez ............... 606/142 |
| 2005/0203605 A1 | 9/2005 | Dolan |
| 2005/0203618 A1 | 9/2005 | Sharkawy |
| 2005/0222674 A1* | 10/2005 | Paine ........................ 623/1.24 |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2005/0288764 A1* | 12/2005 | Snow et al. .................. 623/1.11 |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0064159 A1* | 3/2006 | Porter et al. ................. 623/1.24 |
| 2006/0089711 A1 | 4/2006 | Dolan |
| 2006/0095119 A1* | 5/2006 | Bolduc ........................ 623/1.36 |
| 2006/0100685 A1 | 5/2006 | Seguin et al. |
| 2006/0116757 A1 | 6/2006 | Lashinski et al. |
| 2006/0135964 A1* | 6/2006 | Vesely ......................... 606/108 |
| 2006/0142848 A1 | 6/2006 | Gabbay |
| 2006/0167474 A1 | 7/2006 | Bloom et al. |
| 2006/0173524 A1* | 8/2006 | Salahieh et al. ............ 623/1.11 |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0217802 A1* | 9/2006 | Ruiz et al. ................... 623/2.11 |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265045 A1* | 11/2006 | Shiu et al. .................... 623/1.11 |
| 2006/0265056 A1 | 11/2006 | Nguyen et al. |
| 2006/0271097 A1* | 11/2006 | Ramzipoor et al. .......... 606/200 |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010876 A1* | 1/2007 | Salahieh et al. ............. 623/2.11 |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1* | 2/2007 | Seguin et al. ................ 623/2.11 |
| 2007/0051377 A1 | 3/2007 | Douk et al. |
| 2007/0055340 A1* | 3/2007 | Pryor ........................... 623/1.11 |
| 2007/0061008 A1* | 3/2007 | Salahieh et al. ............. 623/2.11 |
| 2007/0073392 A1 | 3/2007 | Heynick-Jantz |
| 2007/0078509 A1 | 4/2007 | Lotfy et al. |
| 2007/0078510 A1 | 4/2007 | Ryan |
| 2007/0088431 A1* | 4/2007 | Bourang et al. ............. 623/2.11 |
| 2007/0093869 A1 | 4/2007 | Bloom et al. |
| 2007/0100419 A1* | 5/2007 | Licata et al. ................. 623/1.11 |
| 2007/0100439 A1 | 5/2007 | Cangialosi |
| 2007/0100440 A1* | 5/2007 | Figulla et al. ................ 623/2.18 |
| 2007/0100449 A1 | 5/2007 | O'Neil et al. |
| 2007/0112355 A1* | 5/2007 | Salahieh et al. ............. 606/108 |
| 2007/0112415 A1 | 5/2007 | Bartlett |
| 2007/0112422 A1 | 5/2007 | Dehdashtian |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0186933 A1 | 8/2007 | Domingo et al. .......... 128/207.15 |
| 2007/0203391 A1 | 8/2007 | Bloom et al. |
| 2007/0203503 A1* | 8/2007 | Salahieh et al. ............. 606/108 |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0027529 A1* | 1/2008 | Hartley et al. ................ 623/1.11 |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |

(56) References Cited

U.S. PATENT DOCUMENTS

| | | | |
|---|---|---|---|
| 2008/0077234 A1 | 3/2008 | Styrc | |
| 2008/0082159 A1* | 4/2008 | Tseng et al. | 623/1.13 |
| 2008/0082165 A1 | 4/2008 | Wilson et al. | |
| 2008/0082166 A1 | 4/2008 | Styrc et al. | |
| 2008/0133003 A1 | 6/2008 | Seguin et al. | |
| 2008/0140189 A1* | 6/2008 | Nguyen et al. | 623/2.11 |
| 2008/0147105 A1 | 6/2008 | Wilson et al. | |
| 2008/0147180 A1 | 6/2008 | Ghione et al. | |
| 2008/0147181 A1 | 6/2008 | Ghione et al. | |
| 2008/0147182 A1 | 6/2008 | Righini et al. | |
| 2008/0154355 A1 | 6/2008 | Benichou et al. | |
| 2008/0154356 A1 | 6/2008 | Obermiller et al. | |
| 2008/0161910 A1 | 7/2008 | Revuelta et al. | |
| 2008/0161911 A1 | 7/2008 | Revuelta et al. | |
| 2008/0183273 A1 | 7/2008 | Mesana et al. | |
| 2008/0188928 A1 | 8/2008 | Salahieh et al. | |
| 2008/0215143 A1 | 9/2008 | Seguin et al. | |
| 2008/0215144 A1 | 9/2008 | Ryan et al. | |
| 2008/0221666 A1* | 9/2008 | Licata et al. | 623/1.22 |
| 2008/0228254 A1 | 9/2008 | Ryan | |
| 2008/0228263 A1 | 9/2008 | Ryan | |
| 2008/0234797 A1 | 9/2008 | Styrc | |
| 2008/0243246 A1 | 10/2008 | Ryan et al. | |
| 2008/0255651 A1 | 10/2008 | Dwork | |
| 2008/0255660 A1 | 10/2008 | Guyenot et al. | |
| 2008/0255661 A1 | 10/2008 | Straubinger et al. | |
| 2008/0262593 A1 | 10/2008 | Ryan et al. | |
| 2008/0269878 A1 | 10/2008 | Iobbi | |
| 2009/0005863 A1 | 1/2009 | Goetz et al. | |
| 2009/0012600 A1 | 1/2009 | Styrc et al. | |
| 2009/0048656 A1* | 2/2009 | Wen | 623/1.12 |
| 2009/0054976 A1* | 2/2009 | Tuval et al. | 623/2.11 |
| 2009/0069886 A1 | 3/2009 | Suri et al. | |
| 2009/0069887 A1 | 3/2009 | Righini et al. | |
| 2009/0069889 A1 | 3/2009 | Suri et al. | |
| 2009/0082858 A1 | 3/2009 | Nugent et al. | |
| 2009/0085900 A1 | 4/2009 | Weiner | |
| 2009/0099653 A1 | 4/2009 | Suri et al. | |
| 2009/0138079 A1 | 5/2009 | Tuval et al. | |
| 2009/0164004 A1 | 6/2009 | Cohn | |
| 2009/0164006 A1 | 6/2009 | Seguin et al. | |
| 2009/0171447 A1 | 7/2009 | VonSegesser et al. | |
| 2009/0192585 A1 | 7/2009 | Bloom et al. | |
| 2009/0192586 A1 | 7/2009 | Tabor et al. | |
| 2009/0192591 A1 | 7/2009 | Ryan et al. | |
| 2009/0198316 A1 | 8/2009 | Laske et al. | |
| 2009/0216310 A1 | 8/2009 | Straubinger et al. | |
| 2009/0216312 A1 | 8/2009 | Straubinger et al. | |
| 2009/0216313 A1 | 8/2009 | Straubinger et al. | |
| 2009/0222082 A1 | 9/2009 | Lock et al. | |
| 2009/0234443 A1 | 9/2009 | Ottma et al. | |
| 2009/0240264 A1 | 9/2009 | Tuval et al. | |
| 2009/0240320 A1 | 9/2009 | Tuval | |
| 2009/0287296 A1 | 11/2009 | Manasse | |
| 2010/0004740 A1 | 1/2010 | Seguin et al. | |
| 2010/0030328 A1 | 2/2010 | Seguin et al. | |
| 2010/0036479 A1 | 2/2010 | Hill et al. | |
| 2010/0036485 A1 | 2/2010 | Seguin | |
| 2010/0049313 A1* | 2/2010 | Alon et al. | 623/2.11 |
| 2010/0069852 A1 | 3/2010 | Kelley | |
| 2010/0094411 A1 | 4/2010 | Tuval et al. | |
| 2010/0100167 A1 | 4/2010 | Bortlein et al. | |
| 2010/0131054 A1 | 5/2010 | Tuval et al. | |
| 2010/0137979 A1 | 6/2010 | Tuval et al. | |
| 2010/0145439 A1 | 6/2010 | Seguin et al. | |
| 2010/0152840 A1 | 6/2010 | Seguin et al. | |
| 2010/0161045 A1 | 6/2010 | Righini | |
| 2010/0198346 A1 | 8/2010 | Keogh et al. | |
| 2010/0234940 A1 | 9/2010 | Dolan | |
| 2010/0256723 A1 | 10/2010 | Murray | |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/026371 | 3/2006 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | WO 2009/042196 A2 | 4/2009 |
| WO | 2009/061389 | 5/2009 |
| WO | 2009/091509 | 7/2009 |
| WO | 2009/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. Volume II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava A Reliable Technique to Treat Chronic Venous Insufficiency Syndrome?" Medical Science Monitor—International Medical Journal of Experimental and Clinical Research (Poland), Mar. 2004, pp. BR61-BR66.

(56) References Cited

OTHER PUBLICATIONS

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology(Ireland), 2001, pp. 89-93.
Boudjemline, et al, "Transcatheter Reconstruction of the Right Heart," Cardiology in the Young(England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. 1. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vol. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Techol. 2000, vol. 9, pp. 287-292.
European Patent Office Communication in Application No. 09 704 087.7-2320, Dated Nov. 30, 2012, 5 pages.

\* cited by examiner

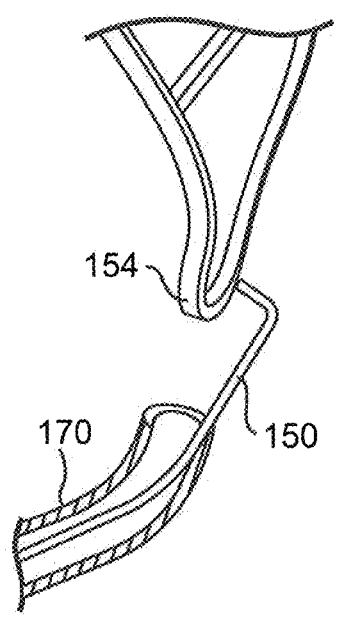 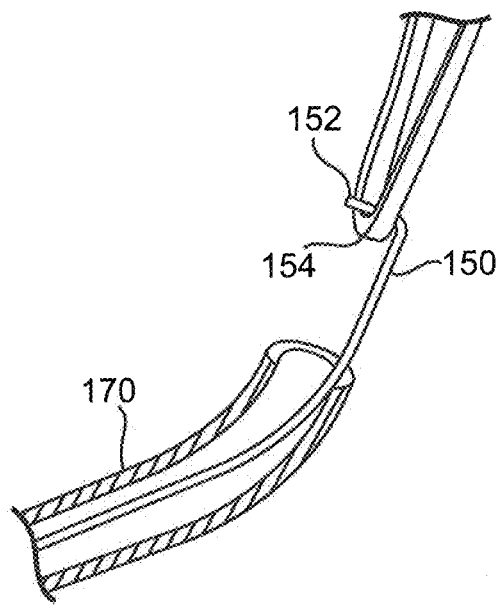
Fig. 14    Fig. 15
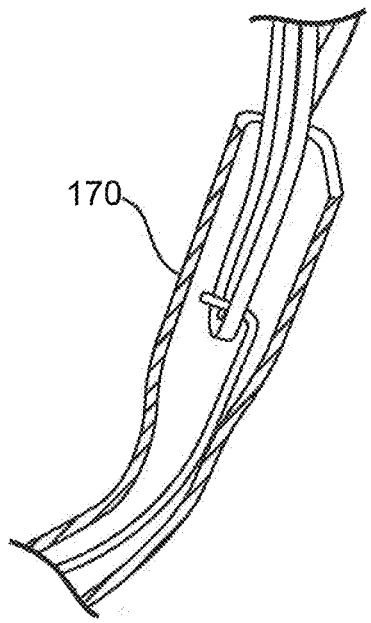
Fig. 16

DELIVERY SYSTEMS FOR PROSTHETIC HEART VALVES

CROSS-REFERENCE TO RELATED APPLICATION

The present application claims priority to U.S. Provisional Application No. 61/062,207, filed Jan. 24, 2008, and titled "Delivery Systems and Methods of Implantation for Prosthetic Heart Valves", the entire contents of which is incorporated herein by reference in its entirety.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a very small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously-delivered prosthetic heart valves and systems for delivering them have been suggested, such as by Bonhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These heart valves and delivery techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons that are sometimes used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Implantable, catheter-based devices, such as heart valves, are often pre-attached to a delivery system in order to simplify the procedure and minimize the degree and amount of clinician handling and associated risks. On the other hand, typical transcatheter valve systems include a valve that is not attached to the delivery system because it is not desirable for the tissue to be compressed in a delivery catheter for long periods of time. Thus, these systems require the clinician to directly handle the implantable valve in order to rinse the bioprosthetic valve and also significantly manipulate both the valve and stent and delivery system in order to attach the valve to the delivery system. This handling and manipulation increases the potential for damage to and/or misassembly of the stent/valve/delivery system, potentially leading to short or long-term consequences that can affect device placement or performance. In addition, direct handling of the valve/stent device by a clinician can increase the potential for contamination, which in turn can lead to patient infection or other serious patient consequences.

Although there have been advances in percutaneous valve replacement techniques and devices, there is a continued desire to provide different designs of cardiac valves that can be implanted in a minimally invasive and percutaneous manner. There is also a continued desire to provide a simplified manner of attaching a stented valve to a delivery system that requires less direct handling by a clinician immediately prior to implantation.

SUMMARY

Replacement heart valves that can be used with delivery systems of the invention each include a stent within which a valve structure can be attached, although it is possible that the delivery systems instead be used for delivery of valveless stents. The stents used with delivery systems and methods of the invention include a wide variety of structures and features that can be used alone or in combination with other stent features. In particular, these stents provide a number of different docking and/or anchoring structures that are conducive to percutaneous delivery thereof. Many of the structures are thus compressible to a relatively small diameter for percutaneous delivery to the heart of the patient, and then are expandable either via removal of external compressive forces (e.g., self-expanding stents), or through application of an outward radial force (e.g., balloon expandable stents). The devices delivered by the delivery systems described herein include stents, valved stents, or other interventional devices such as atrial septal defect closure devices, ventricular septal defect closure devices, or patent foramen ovale occluders.

Methods for insertion of the replacement heart valves of the invention include delivery systems that can maintain the stent structures in their compressed state during their insertion and allow or cause the stent structures to expand once they are in their desired location. In particular, the methods of the invention for implanting a stent can include the use of delivery systems having a cartridge that can be pre-attached to a stent. The cartridge and stent can be provided to the operator in such a way that when the operator attaches the cartridge to the remainder of the delivery system, the delivery system will be ready for the surgical valve implantation procedure. Because the stent is preloaded on the cartridge, this approach can thereby eliminate or greatly reduce the time that is otherwise normally spent in the surgical area attaching a stent to a delivery system. The cartridge concept simplifies the attachment of the valve to the delivery system, improves the reliability and consistency of the attachment and prevents the undesirable consequences that can occur if the valve is attached backwards onto the delivery system. In addition the cartridge approach provides a surface for the clinician to grasp the implant during the valve rinsing process, thereby alleviating the need for direct contact with the implantable valve/stent during the valve rinsing process.

In one embodiment, the cartridge has a first or distal end to which the stent is attached and a second or proximal end that is attachable to the delivery system using one of a number of different connection configurations. The cartridge of the invention can also include sleeves or other devices for securing the stent to the cartridge after the initial attachment of these components. In addition, delivery methods of the invention can include features that allow the stents to be retrieved for removal or relocation thereof after they have been deployed or partially deployed from the stent delivery systems. The methods may include implantation of the stent structures using either an antegrade or retrograde approach. Further, in many of the delivery approaches of the invention, the stent structure is rotatable in vivo to allow the stent structure to be positioned in a desired orientation.

BRIEF DESCRIPTION OF THE DRAWINGS

The present invention will be further explained with reference to the appended Figures, wherein like structure is referred to by like numerals throughout the several views, and wherein:

FIGS. 14-16 are enlarged perspective views of a configuration for attaching a stent to a wire having a hook at its distal end.

DETAILED DESCRIPTION

Figure 1:
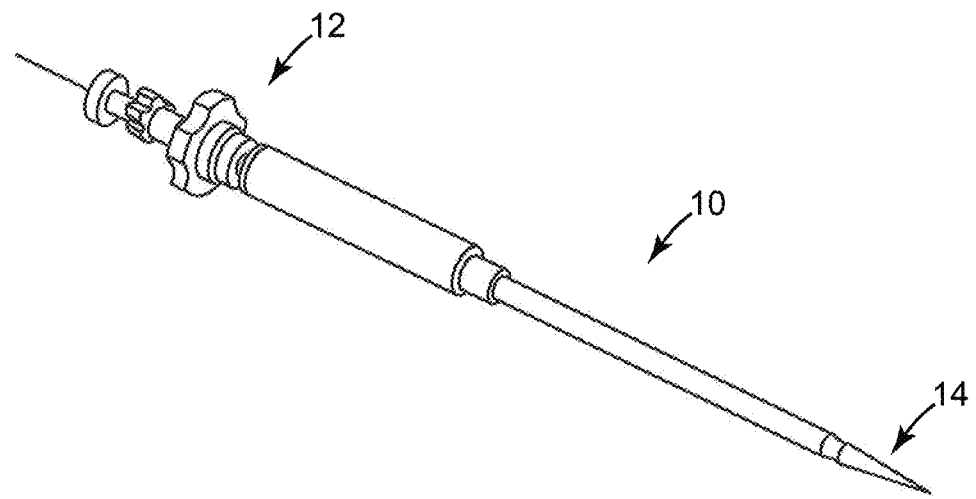
FIG. 1 is a perspective view of one embodiment of a delivery system of the invention.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

As referred to herein, the prosthetic heart valves used in accordance with the various devices and methods of heart valve delivery may include a wide variety of different configurations, such as a prosthetic heart valve having tissue leaflets or a synthetic heart valve having polymeric, metallic, or tissue-engineered leaflets, and can be specifically configured for replacing any heart valve. That is, while much of the description herein refers to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example.

Although each of the prosthetic valves used with the delivery devices and methods described herein would typically include leaflets attached within an interior area of a stent, for clarity purposes, such leaflets are not shown in the illustrated embodiments. In general, the stents used with the delivery systems and methods described herein include a support structure comprising a number of strut or wire portions arranged relative to each other to provide a desired compressibility and strength to the heart valve. Although a number of different configurations of stents can be used, in general terms, the stents described herein are generally tubular support structures within which leaflets can be secured to provide a valved stent. The leaflets can be formed from a variety of materials, such as autologous tissue, xenograph material, or synthetics, as are known in the art. The leaflets may be provided as a homogenous, biological valve structure, such as a porcine, bovine, or equine valve. Alternatively, the leaflets can be provided as independent structures (e.g., bovine or equine pericardial leaflets) that are subsequently assembled to the support structure of the stent. In another alternative, the stent and leaflets can be fabricated at the same time, such as may be accomplished using high strength nano-manufactured NiTi films of the type produced by Advanced Bio Prosthetic Surfaces Ltd. (ABPS) of San Antonio, Tex., for example. The support structures are generally configured to accommodate three leaflets; however, the replacement prosthetic heart valves described herein can incorporate more or less than three leaflets.

In more general terms, the combination of a support structure with one or more leaflets can assume a variety of other configurations that differ from those shown and described, including any known prosthetic heart valve design. In certain embodiments of the invention, the support structure with leaflets can be any known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodyamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000:102: 813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Optional orientation and positioning of the stents of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. For example, when aligning the stents of the invention with native anatomical structures, they should be aligned so as to not block the coronary arteries, and native mitral or tricuspid valves should be aligned relative to the anterior leaflet and/or the trigones/commissures.

The wires of the support structures of stents can be formed from a shape memory material such as a nickel titanium alloy (e.g., Nitinol). With this material, the support structure is self-expandable from a contracted state to an expanded state, such as by the application of heat, energy, and the like, or by the removal of external forces (e.g., compressive forces provided by a sheath). This support structure can be compressed and re-expanded without damaging the structure of the stent. In addition, the support structure of such an embodiment may be laser cut from a single piece of material or may be assembled from a number of different components. For these types of stent structures, one example of a delivery system that can be used includes a catheter with a retractable sheath that covers the stent until it is to be deployed, at which point the sheath can be retracted to allow the stent to expand.

The stents can alternatively be a series of wires or wire segments arranged so that they are capable of transitioning from a collapsed state to an expanded state only with the application of some type of force (e.g., an internal radial force pressing the stent outwardly). The wires comprising the support structure can be formed of a metal or other material. Further, these wires are arranged in such a way that allows for folding or compressing the stent to a contracted state in which its internal diameter is greatly reduced from when the structure is in an expanded state. When such a support structure (which preferably has an attached valve) is in its collapsed state, it can be mounted over a delivery device, such as a balloon catheter, for example. The support structure is configured so that it can be converted to its expanded state when desired, such as by the expansion of a balloon catheter. The delivery systems used for such a stent can be provided with degrees of rotational and axial orientation capabilities in order to properly position the new stent at its desired location.

Referring now to the Figures, wherein the components are labeled with like numerals throughout the several Figures, and initially to FIGS. 1-6, one embodiment of a stent delivery system is illustrated. This system includes a cartridge for initial attachment of a stent and/or stent device to a stent base device and subsequent attachment of the cartridge and attached stent to the delivery system, thereby providing quick and simple attachment of a stent to a delivery system by an operator. In this embodiment of the invention, the attachment mechanism is a dovetail type of arrangement, which includes a mating feature on both a cartridge and a delivery system that allows the stent and cartridge to be preloaded and easily attached to the delivery system. Other mechanical attachment mechanisms can instead be used in place of the dovetail connection, such as threaded members, snap-fit connections, frictional connections, pins, and magnetic connections, for example.

Figure 2:
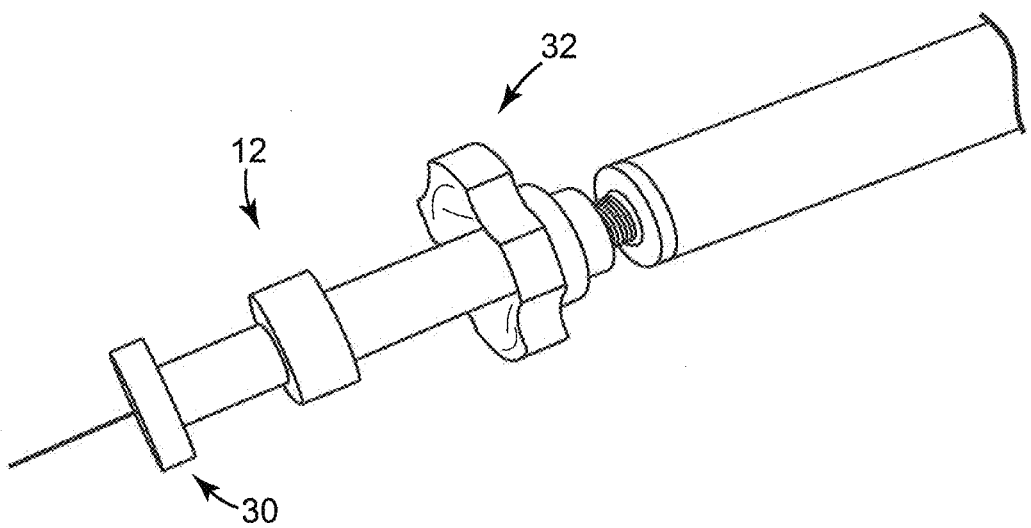
FIG. 2 is a perspective view of a proximal end of the delivery system illustrated in FIG. 1.

In particular, FIG. 1 illustrates one exemplary delivery system 10 that generally includes a proximal end 12 and a distal end 14. FIG. 2 shows an enlarged view of the proximal end 12 of the delivery system 10 of FIG. 1. Proximal end 12 includes a first knob 30 and a second knob 32 for use in controlling the delivery and deployment of a stent at the generally distal end 14, as will be described in further detail below. A delivery system for percutaneous stent and valve delivery can comprise a significantly longer delivery system that can be maneuvered through a patient's vasculature until a desired anatomical location is reached. In any case, the delivery system can include features that allow it to deliver a stent to a desired location in a patient's body.

Figure 3:
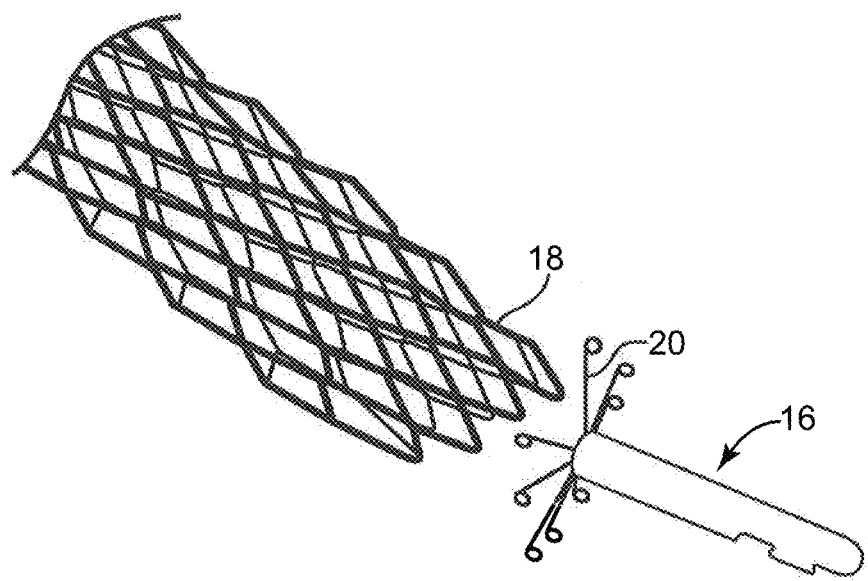
FIG. 3 is a perspective view of a cartridge having plural wires with coiled ends as the wires are being attached to a stent frame.
Figure 4:
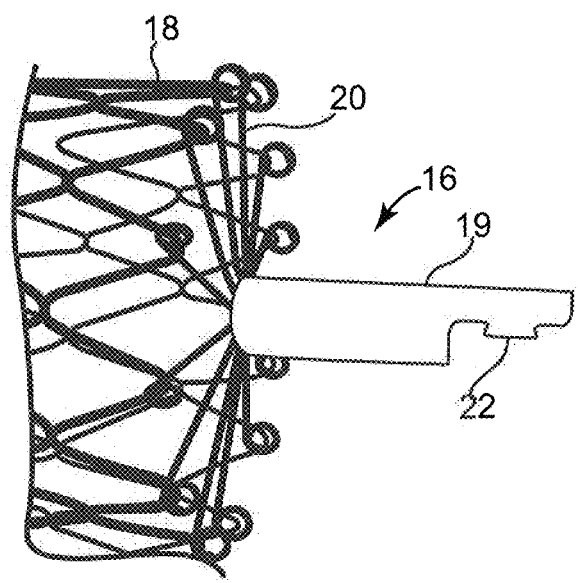
FIG. 4 is an enlarged side view of the cartridge of FIG. 3 attached to the crowns at one end of a stent.

A cartridge 16 is illustrated in FIG. 3 adjacent to an exemplary wire stent 18 to which it will be attached, is shown in FIG. 4. The cartridge 16 includes a post 19 having a series of wires 20 extending from one end and a dovetail attachment portion 22 at the opposite end. Each of the wires 20 can be a spring wire that is formed at its distal end into a coiled or "pigtail" configuration and includes a generally straight portion that is connected to the post 19 at its proximal end. Each wire 20 is made of a shape-memory type of material (e.g., Nitinol) that can be straightened by applying an external force when in the proximity of a stent to which it will be attached and that will return generally to its coiled configuration when the straightening force is removed. Alternatively, the wires can be somewhat malleable so that they do not necessarily return to their original coil shape once stented valve features have been released from the wire. The size and exact configuration of the pigtail end portion of each wire can be chosen or designed so that the forces required to retract and deploy the stent are within a desirable range.

In order to load a stent onto the wires 20 of cartridge 16, the coiled or pigtail portions of each wire 20 can be straightened or partially straightened and placed adjacent to one of the crowns or "V" ends of the stent. The force on each wire 20 can then be removed or reduced so that the distal end of the wire coils back toward its pigtail configuration, thereby wrapping around and capturing one crown of the stent 18, as shown in FIG. 4. The wire can be made of spring materials or shape memory materials that may be cured or "set" via a heat treating process so that the coiled wire end can be retracted, clocked, redeployed, disengaged, or the like, without the use of additional tools or the management of removed parts. If a different stent construction is used, the coiled wires can instead engage with some other feature of that type of stent. One wire having a pigtail or coiled wire end is preferably provided for each of the crowns of the stent, although the cartridge can be provided with more or less wires having coiled ends. It is also contemplated that a single crown of a stent may have more than one pigtail wire attached to it. After the wires 20 of the cartridge 16 are attached to the stent 18, the cartridge and stent combination can be considered to be "loaded" and is then ready for attachment to the delivery system 10.

In one method of the present invention, the process of attaching a stent to the cartridge can be performed immediately prior to the surgery during which the sent will be implanted in the patient. In this case, the valved stent can be attached in the operating room or its general proximity at approximately the same time that the clinician is preparing to implant the valved stent. Alternatively, the attachment of a valved stent to the cartridge can occur at a remote time and/or place relative to the time and location of the implantation. For example, the valved stent can be pre-attached to a cartridge, and then the valved stent and cartridge can be packaged together within a gluteraldehyde solution and provided in a pre-assembled manner to a clinician. In this way, the clinician can simply remove the assembly at the time of the implantation procedure and attach it to the delivery system, which can reduce the amount of time the valved stent needs to be manipulated immediately prior to the time of implantation. This attachment of a stent to the cartridge can be performed at any appropriate period of time prior to the implantation procedure, as long as the quality of the valve material remains acceptable The exemplary stent 18, one end of which is shown in the Figures, is made of a series of wires that are compressible and expandable through the application and removal of external forces, and may include a series of Nitinol wires that are approximately 0.011-0.015 inches in diameter, for example. That is, the stent 18 may be considered to be a self-expanding stent. However, the stent to which the coiled wire portions of the cartridge are attached can have a number of different configurations and can be made of a wide variety of different materials.

Figure 5:
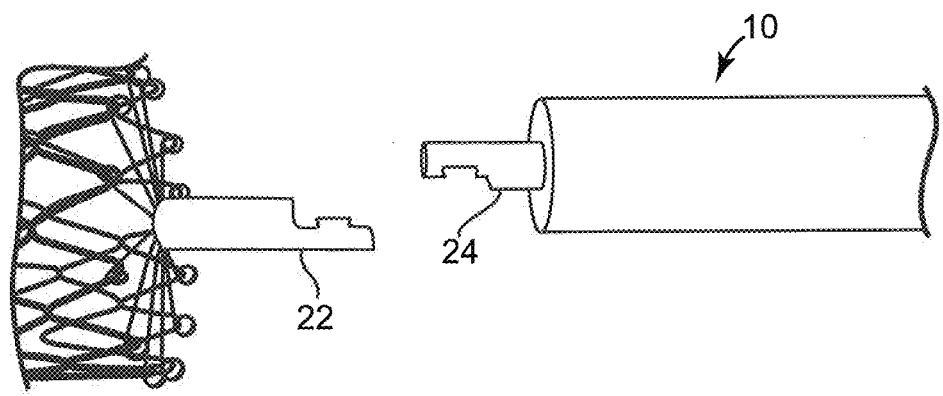
FIG. 5 is a side view of the cartridge and attached stent of FIG. 4 in proximity to a portion of a delivery system to which they will be attached.

FIG. 5 illustrates one end of the delivery system 10 as having a dovetail notch portion 24 that can mate or attach to a corresponding dovetail tab portion 22 of the cartridge 16. To attach the components to each other, the tab portion 22 is slid into the notch portion 24 until these two components are sufficiently engaged with each other so that manipulation of the delivery system will not cause them to become disengaged from each other. A dovetail configuration is one exemplary engagement mechanism of the cartridges of the invention. Other mechanical arrangements of cooperating elements on two portions of a delivery system can instead be used, some of which are described below. In general terms, however, the stent structure is attached to a cartridge, which in turn is mechanically attachable to another piece of the delivery system.

Figure 6:
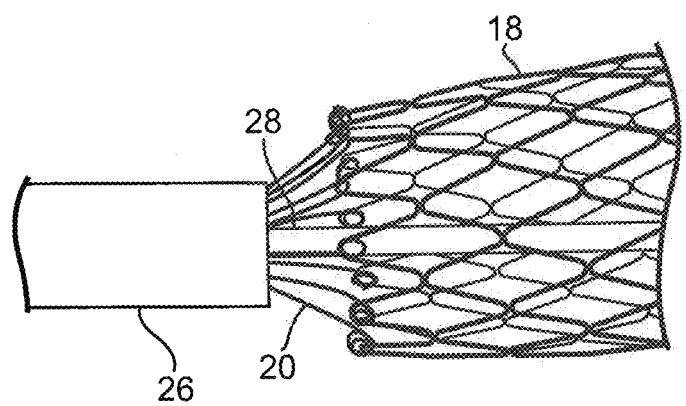
FIG. 6 is a side view of a delivery system of the invention with an attached stent.

As shown in FIG. 6, after the cartridge is attached to the delivery system, the cartridge and its attached stent can then be retracted into a hollow tube or lumen 26 of the delivery system by moving or pulling the cartridge toward the proximal end of the delivery device. This movement is continued until the crowns of the stent 18 are adjacent to the end of the lumen 26. Due to the compressible nature of the stent 18, continued movement of the cartridge 16 toward the proximal end of the delivery device will pull the wires 20 toward a central lumen 28 of the delivery system, thereby also moving the wires of the stent 18 toward the central lumen 28 (i.e., compressing the stent). The lumen 26 can then continue to be moved toward the proximal end of the device until the stent 18 is completely enclosed within the lumen 26, as illustrated in FIG. 1.

The delivery system can then be used to deliver the stent 18 to its desired location in a lumen (e.g., a heart valve area) of a patient and deploy the valved stent. In one deployment method, the lumen 26 can be moved away from a distal tip of the delivery system to expose the free end of the stent 18. As the lumen is moved in this way, the compressive forces that were provided by the lumen are removed so that the stent 18 is allowed to expand outwardly. The wires 20 are then manipulated via an actuating mechanism of the delivery system until they are sufficiently uncoiled or straightened so that they become disengaged from the stent 18, thereby deploying the stent. The delivery system can then be removed from the patient and the cartridge 16 can be disconnected from the remainder of the delivery system, if desired, by disconnecting the tab attachment portion 22 and the notch portion 24.

With this system described above, full or partial blood flow through the valve can advantageously be maintained during the period when the stented valve is being deployed into the patient but is not yet released from its delivery system. This feature can help to prevent complications that may occur when blood flow is stopped or blocked during valve implantation with some other known delivery systems. In addition, it is possible for the clinician to thereby evaluate the opening and closing of leaflets, examine for any paravalvular leakage and evaluate coronary flow and proper positioning of the valve within the target anatomy before final release of the stented valve.

The process of pulling the wires toward the lumen in many of the described embodiments of the invention can be accomplished in a number of ways, such as by rotating the device over coarse threads or pushing a button to slide it to pull the wires toward the lumen. That is, a number of different mechanisms can be used to accomplish this movement of the wires relative to the delivery system. Further, it is noted that while the coiled wire ends described herein are generally shown to be engaging with the end crowns of a stent, the coiled wire ends can instead engage with intermediate stent crowns or other stent features.

Figure 7:
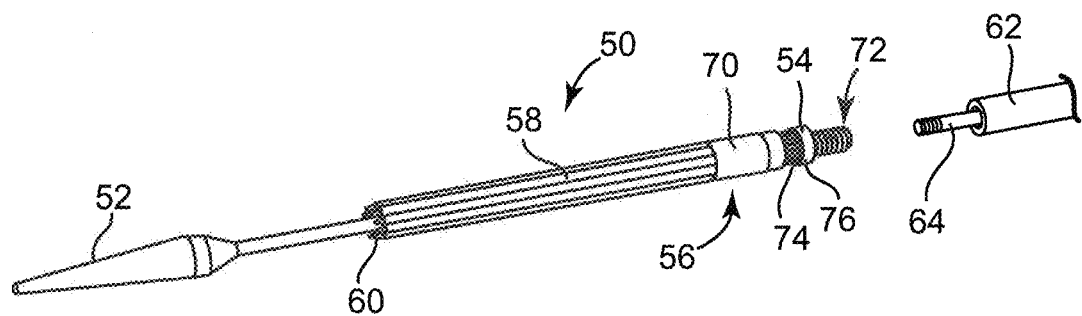
FIG. 7 is a perspective view of one configuration of another cartridge of the invention in proximity to a portion of a delivery system to which it will be attached.
Figure 8:
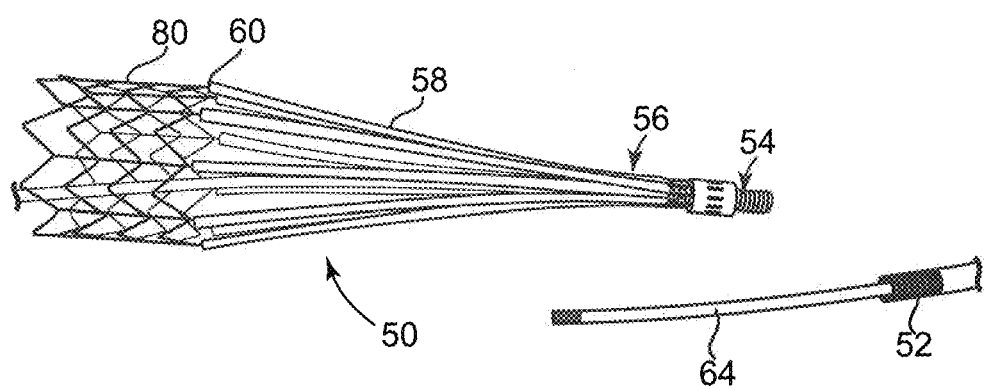
FIG. 8 is a side view of a cartridge of the invention with a stent attached to its distal end.

Another exemplary embodiment of a delivery system of the invention, which includes a cartridge 50, is illustrated in FIGS. 7 through 13. With particular reference to FIGS. 7 and 8, cartridge 50 generally includes a distal or dilator tip 52, a proximal end 72, a hook assembly 54 adjacent to the proximal end 72, and a sleeve assembly 56 generally adjacent to the hook assembly 54. Sleeve assembly 56 includes a base portion 70 and multiple sleeves 58 that extend from the base portion 70 toward the distal tip 52. The sleeves 58 are shown in a compressed configuration in FIG. 7, which is the general position the sleeves 58 will be in when they are being held within a sleeve during the process of being delivered into a body lumen, for example. FIG. 8 shows the sleeves 58 in a splayed or expanded configuration, such as would be the case when a sleeve or similar mechanism is not compressing the sleeves 58 toward a central axis of the delivery system. In this configuration, a proximal end of each of the sleeves 58 is attached to the base portion 70, while a distal end of each sleeve 58 is free to move away from the central axis of the delivery system. The proximal end of the sleeves 58 may be surrounded or partially surrounded by a collar or cover to secure the sleeves 58 to the base portion 70. Each of the sleeves 58 has an elongated tubular construction and is designed to surround the outer diameter of a straight portion of a wire of the hook assembly 54, which is described in further detail below.

Hook assembly 54 includes a base portion 76 from which multiple wires 74 extend. Each of the wires 74 are attached at a proximal end to the base portion 76 and terminate at a hook 60 at a distal end. As shown, each hook 60 extends from the distal end of a corresponding sleeve 58. The hooks 60 are designed for engagement with wires or another structure of a stent, where an exemplary stent 80 is shown in FIG. 8 as being attached to such hooks 60. The hooks 60 can have a wide variety of configurations, such as angled, curved, and the like, and should be positioned for engagement with some structure feature or features of the stent 80. In one embodiment of the invention, the number of hooks 60 that are provided is the same as the number of crowns on a corresponding stent so that each hook can be engaged with one stent crown; however, the number of hooks and stent crowns can be different and/or the hooks can be configured for engagement with a different structure of the stent than its crowns.

The delivery system further includes a hook holding tube 62 from which an inner actuation tube 64 extends. The inner actuation tube 64 includes an external threaded portion on its distal end. In order to engage with the hook holding tube 62, the cartridge 50 further includes an internal threaded portion within the sleeve assembly 56 and an external thread on the outside of the hook assembly 54. In this way, the external threaded portion of the inner actuation tube 64 can engage with the internal threaded portion of the sleeve assembly 56. Further, the hook holding tube 62 includes an internal threaded portion at its distal end that can engage with the external thread of the hook assembly 54.

Figure 9:
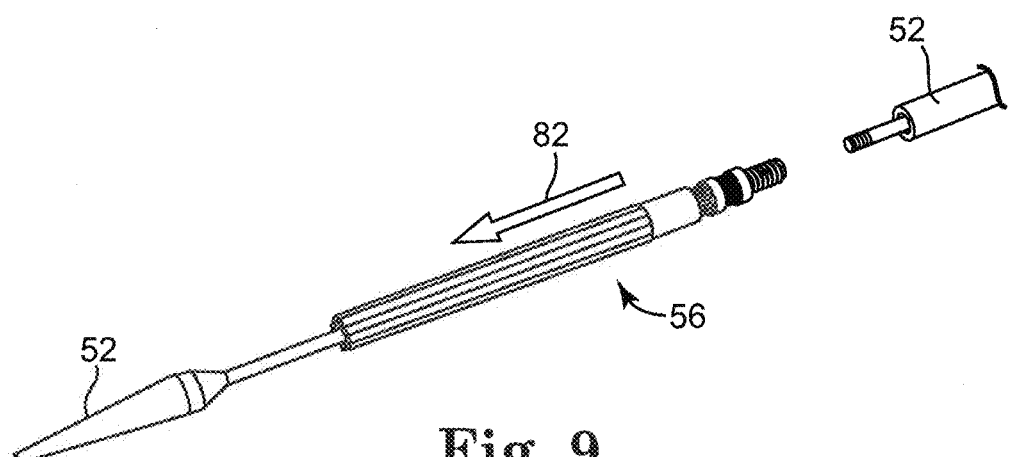
FIG. 9 is a perspective view of the cartridge of FIG. 7, with the components in another configuration relative to each other.
Figure 10:
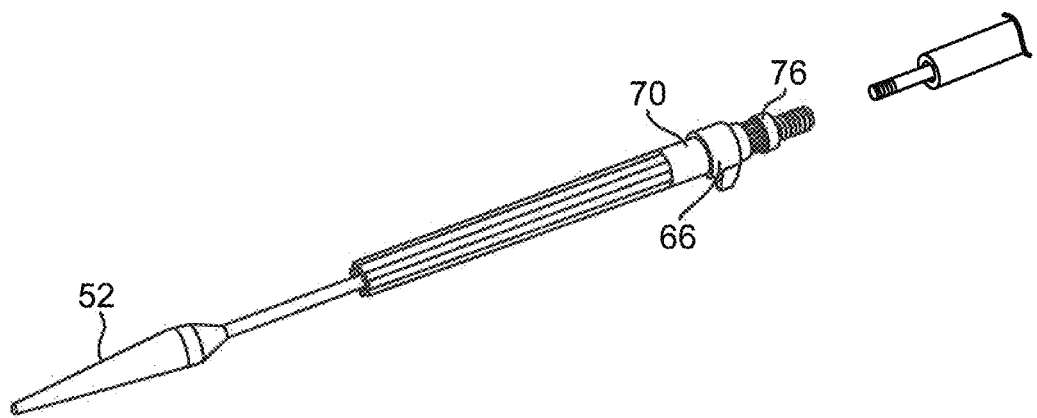
FIG. 10 is another perspective view of the cartridge of FIG. 7, with the components in yet another configuration relative to each other.

In order to attach a stent to the cartridge 50, the hooks 60 are positioned for engagement with a structure of the stent, such as the crowns of a stent, as is described above. In order to further secure the hooks 60 to these stent structures, the sleeve assembly 56 can be slid in a direction 82 toward the distal end of the cartridge 50, as illustrated in FIG. 9. The sleeves 58 are preferably made of a relatively expandable material so that each sleeve can deform at least slightly as it slides over a corresponding hook 60, thereby capturing or enclosing the stent and the hook within the sleeve 58. As illustrated in FIG. 10, a sleeve lock 66 can then be slid into the space between the base 70 of sleeve assembly 56 and the base 76 of hook assembly 54, and locked or snapped into place around the cartridge. The sleeve lock 66 is designed to prevent the sleeve assembly 56 from sliding back toward the proximal end of the cartridge 50, thereby keeping the hooks 60 captured within the sleeves 58. Alternatively, another mechanism can be used to keep the sleeves 58 from becoming disengaged from the hooks 60, such as a spring that is positioned on the cartridge in such a way that the sleeve assembly 56 cannot move relative to the hook assembly 54.

Figure 11:
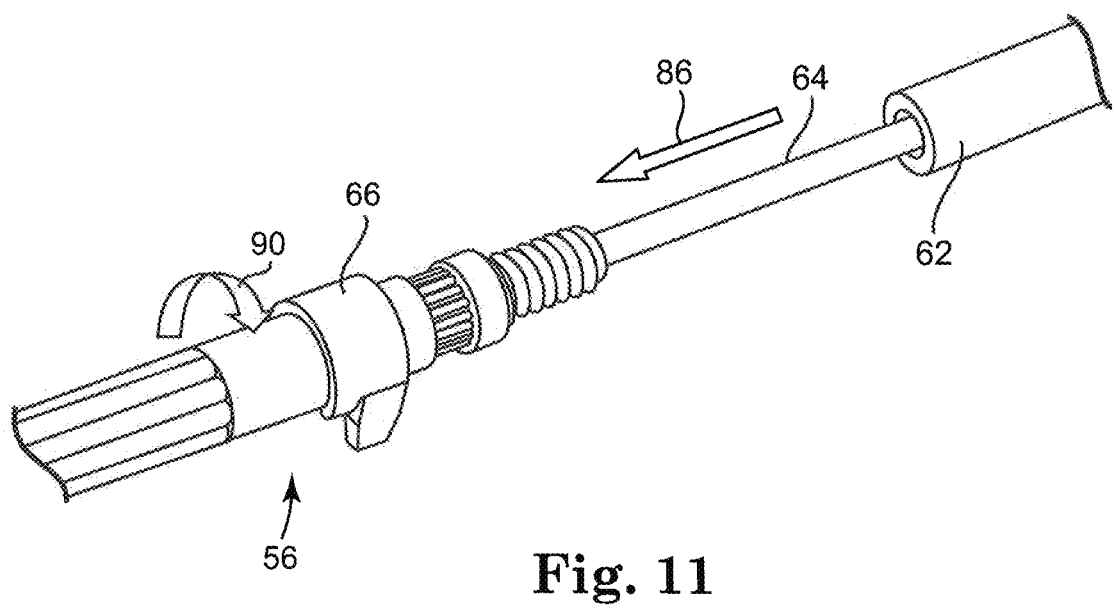
FIG. 11 is an enlarged perspective view of a portion of the cartridge of FIG. 10.
Figure 12:
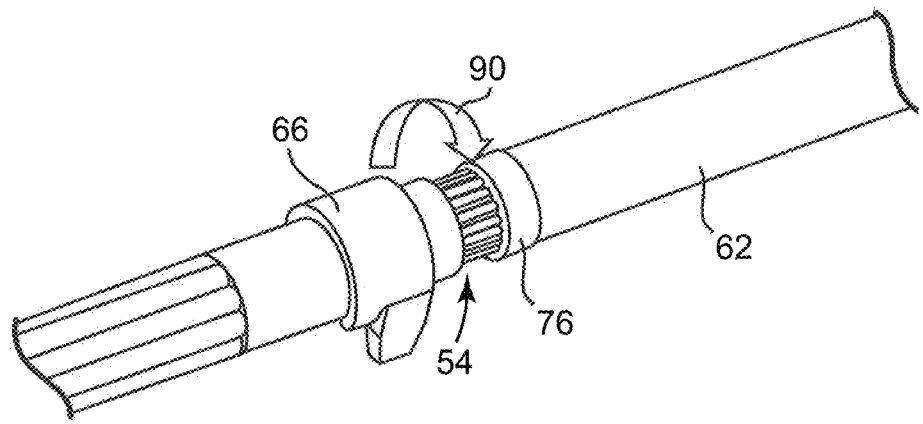
FIG. 12 is another view of the cartridge of FIG. 11.

After the stent 80 is attached to the cartridge 50 as described above, the cartridge 50 can be attached to the distal end of a delivery system. Referring in particular to FIGS. 11 and 12, the cartridge 50 is attachable to the hook holding tube 62 and inner actuation tube 64 of a delivery system by guiding the distal end of the inner actuation tube 64 through the center hole of the hook assembly 54. This movement of the inner actuation tube 64 is shown as being in a direction generally indicated by arrow 86. The inner actuation tube 64 can be moved in this direction 86 until it contacts the internal threads of the sleeve assembly 56. The inner actuation tube 64 is then held stationary while the sleeve assembly 56 is rotated in a direction indicated by arrow 88 until the components are securely engaged with each other. It is possible, however, that the inner actuation tube is instead rotated relative to a stationary sleeve assembly 56 or that both the sleeve assembly 56 and the inner actuation tube 64 are rotated in opposite directions relative to each other. Any guidewire lumens provided on the dilator tip 52 and the inner actuation tube 64 should be aligned and in contact when fully engaged.

Next, the hook holding tube 62 is pulled distally until it contacts the base 76 of the hook assembly 54, as shown in FIG. 12. The hook assembly 54 can then be held in place while the hook holding tube 62 is rotated, such as in a direction indicated by the arrow 90. Again, it is possible that the hook holding tube 62 is instead rotated relative to the hook assembly 54 that is being held stationary, or that both the hook holding tube 62 and the hook assembly 54 are rotated in opposite directions from each other. The rotation of the hook holding tube 62 and hook assembly 54 relative to each other can continue until the threads are fully engaged and so that the hook assembly 54 is being held by the hook holding tube 62.

Figure 13:
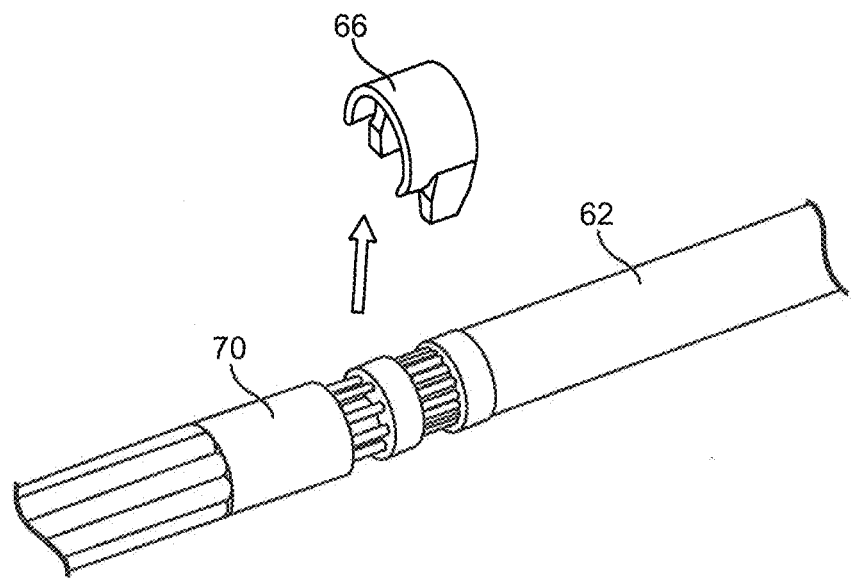
FIG. 13 is yet another view of the cartridge of FIG. 11, but with the sleeve lock removed.

Referring now to FIG. 13, the sleeve lock 66 can then be removed from the assembly. At this point, sliding the inner actuation tube 64 will cause the sleeve assembly 56 to also slide. The proximal end of the inner actuation tube 64 can then be attached to any number of actuation devices, such as a thumb slide, screw drive, or the like. The actuation device or devices that are chosen can be located within a handle, for example.

Although the description above primarily discusses threaded engagement of the various components to each other, other types of engagement methods and configurations can be used. For example, the components can be connected to each other using snap-fit connections, frictional fittings, other quick-connect methods, and/or other methods or combinations of methods can be used.

The delivery systems of the invention, which include a stent attached to a cartridge, can be delivered through a percutaneous opening (not shown) in a patient. The implantation location can be located by inserting a guide wire into the patient, which guide wire extends from a distal end of the delivery system. The delivery system is then advanced distally along the guide wire until the stent is positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the invention, the stent can include a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

FIGS. 14-16 illustrate another exemplary configuration for attaching a stent to the distal hooks of a cartridge. In particular, one wire or element 150 with an angled wire tip or protrusion 152 is shown, although it is understood that the same principles described relative to this element can be equally applied to all of the elements within a single delivery system. In this configuration, a sleeve 170 is positioned over the relatively straight portion of wire or element 150, but retracted relative to its angled wire tip 152 when the element 150 is not engaged with the stent crown 154, as shown in FIG. 14. Once the element 150 is engaged with the stent crown 154, as illustrated in FIG. 15, the sleeve 170 can be slid toward the stent crown 154 until it encases both the end of the stent crown 154 and the angled wire tip or protrusion 152, thereby providing a more secure positioning of the components relative to each other. The sleeve 170 is preferably made of a relatively flexible material that can deform and expand as it slides over the stent crown and angled wire tip 152. This sleeve 170 prevents disengagement of the angled wire tip 152 from its respective stent crown 154, as described above relative to FIGS. 7-13. Other alternative retaining arrangements for connection of a stent to a cartridge may also be used in accordance with the invention, such as sutures that each attach to one or more wires of a stent and/or other hook end configurations, for example.

Once the stent is loaded onto a delivery system, a driver mechanism of the delivery system can be activated to compress the stent and pull it into an outer lumen or tube. This may be accomplished in one exemplary embodiment by rotating a screw mechanism or by sliding the outer lumen over the stent. Once the stent is enclosed within the outer lumen, the loading fixture can be removed by sliding it over the distal end of the delivery device. The delivery device would now be ready for implantation of the valve within a patient.

It is noted that the aspect ratio of certain portions of the stent can be somewhat different from that shown relative to the stent embodiments of the invention. For one particular example, the overall stent length can be shorter so that when the stent is positioned within a patient, the outflow end will be below the sinotubular junction. It is further noted that if the stent of any of the embodiments is to be positioned to replace the aortic valve, the stent can be provided with a lower density wire portion in the area where the coronaries are located. To eliminate the need to clock the device, reduced wire density around the entire perimeter of the stent can be provided. Further, stent embodiments described herein may be modified to include additional structure for attachment of tissue for the valve, such as the vertical stent posts described in many of the embodiments.

A stent attached to a delivery system via a cartridge of the invention can be delivered percutaneously to an implantation location. The cartridge may be designed for use with a stent that is self-expanding, as is shown in FIGS. 7-13. Alternatively, the cartridge shown in the Figures can be modified to include a balloon and appropriate fittings for the balloon so that a balloon-expandable stent can also be used with the cartridge systems of the invention. A delivery system for a balloon-expandable stent generally can include a transcatheter assembly, including a delivery catheter, a balloon catheter, and a guide wire. Some delivery catheters of this type are known in the art, and define a lumen within which the balloon catheter is received. The balloon catheter, in turn, defines a lumen within which the guide wire is slideably disposed. Further, the balloon catheter includes a balloon that is fluidly connected to an inflation source. It is noted that if the stent being implanted is the self-expanding type of stent, the balloon would not be needed and a sheath or other restraining means would be used for maintaining the stent in its compressed state until deployment of the stent, as described herein. In any case, for a balloon-expandable stent, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of the transcatheter assembly.

Prior to delivery, the stent is mounted over the balloon in a contracted state to be as small as possible without causing permanent deformation of the stent structure. As compared to the expanded state, the support structure is compressed onto itself and the balloon, thus defining a decreased inner diameter as compared to an inner diameter in the expanded state. While this description is related to the delivery of a balloon-expandable stent, the same basic procedures can also be applicable to a self-expanding stent, where the delivery system would not include a balloon, but would preferably include a sheath or some other type of configuration for maintaining the stent in a compressed condition until its deployment.

With the stent mounted to the balloon, the transcatheter assembly is delivered through a percutaneous opening (not shown) in the patient via the delivery catheter. The implantation location is located by inserting the guide wire into the patient, which guide wire extends from a distal end of the delivery catheter, with the balloon catheter otherwise retracted within the delivery catheter. The balloon catheter is then advanced distally from the delivery catheter along the guide wire, with the balloon and stent positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the invention, the stent includes a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

Once the stent is properly positioned, the balloon catheter is operated to inflate the balloon, thus transitioning the stent to an expanded state. Alternatively, where the support structure is formed of a shape memory material, the stent can self-expand to its expanded state.

The present invention has now been described with reference to several embodiments thereof. The entire disclosure of any patents, patent applications, publications and journal articles identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A delivery system for delivery of an implantable stented device to a body lumen, the device comprising a plurality of structures at a proximal end of the device, wherein the delivery system comprises:
   a first body portion comprising an outer tube from which an inner actuation member extends, the inner actuation member being slidable relative to the outer tube and comprising a distal end; and
   a second body portion removably attached to the first body portion, wherein the second body portion comprises;
      a wire assembly including a wire base portion and a plurality of wires extending distally from the base portion, wherein each wire comprises a distal end for attachment to the plurality of structures at the proximal end of the stented device, the outer tube of the first body portion being configured to removably engage the wire assembly, and
      a sleeve assembly including a sleeve base portion and a plurality of sleeves, each of the plurality of sleeves at least partially surrounding one of the wires and being axially slideable relative to the distal end of the wire that it surrounds, the inner actuation member of the first body portion being configured to removably engage the sleeve assembly,
   wherein with the outer tube engaged with the wire assembly and the inner actuation member engaged with the sleeve assembly, movement of the inner actuation member relative to the outer tube causes each of the plurality of sleeves to axially slide relative to the distal end of the wire it surrounds.

2. The delivery system of claim 1, wherein the device comprises a stented valve.

3. The delivery system of claim 2, wherein the plurality of structures at the proximal end of the stented valve comprises a plurality of stent crowns.

4. The delivery system of claim 1, wherein the removable attachment between the first and second body portions comprises a threaded connection.

5. The delivery system of claim 4, wherein the distal end of the inner actuation member comprises an external threaded portion and is configured to removably engage with an internal threaded portion of the sleeve assembly.

6. The delivery system of claim 5, wherein the outer tube includes an internal engagement surface for engagement with an external engagement surface of the wire assembly.

7. The delivery system of claim 6, wherein the internal engagement surface of the outer tube is a threaded engagement surface and the external engagement surface of the wire assembly is a threaded engagement surface.

8. The delivery system of claim 1, wherein the removable connection between the first and second body portions comprises a frictional connection.

9. The delivery system of claim 1, wherein the second body portion comprises a cartridge.

10. The delivery system of claim 1, wherein at least one of the plurality of wires comprises a coiled distal end that is removeably attachable to one of the structures of the stented device.

11. The delivery system of claim 1, wherein the outer tube includes an internal engagement surface for engagement with an external engagement surface of the wire assembly.

12. The delivery system of claim 11, wherein the internal engagement surface of the outer tube is a threaded engagement surface and the external engagement surface of the wire assembly is a threaded engagement surface.

13. The delivery system of claim 1, further comprising a sheath surrounding the outer tube and the stented device for maintaining the stented device in a radially compressed configuration.

* * * * *